(12) United States Patent
Katou et al.

(10) Patent No.: US 9,244,048 B2
(45) Date of Patent: Jan. 26, 2016

(54) GAS SENSOR AND SUBASSEMBLY UNIT THEREFOR

(75) Inventors: Hidekazu Katou, Ichinomiya (JP); Masataka Taguchi, Konan (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 301 days.

(21) Appl. No.: 13/881,655

(22) PCT Filed: Jan. 12, 2012

(86) PCT No.: PCT/JP2012/000146
§ 371 (c)(1),
(2), (4) Date: Apr. 25, 2013

(87) PCT Pub. No.: WO2012/111245
PCT Pub. Date: Aug. 23, 2012

(65) Prior Publication Data
US 2013/0205872 A1  Aug. 15, 2013

(30) Foreign Application Priority Data
Feb. 16, 2011 (JP) ................................. 2011-030748

(51) Int. Cl.
*G01N 33/00* (2006.01)
*G01N 27/407* (2006.01)

(52) U.S. Cl.
CPC ........ *G01N 33/0009* (2013.01); *G01N 27/4077* (2013.01)

(58) Field of Classification Search
CPC . H01R 13/41; H01R 13/4223; G01N 33/0009
USPC .......... 73/31.07; 439/733.1, 752.5, 725, 869, 439/883
See application file for complete search history.

(56) References Cited

U.S. PATENT DOCUMENTS

| 5,489,222 A * | 2/1996 | Moyer et al. ................... 439/748 |
| 2007/0243760 A1* | 10/2007 | Fujita et al. .................... 439/585 |
| 2008/0032570 A1* | 2/2008 | Hitomi et al. .................. 439/883 |

FOREIGN PATENT DOCUMENTS

| JP | 2007-278806 A | 10/2007 |
| JP | 2007-285769 A | 11/2007 |
| JP | 2008-76289 A | 4/2008 |
| JP | 2008-286731 A | 11/2008 |

* cited by examiner

*Primary Examiner* — Peter Macchiarolo
*Assistant Examiner* — Alexander Mercado
(74) *Attorney, Agent, or Firm* — Sughrue Mion, PLLC

(57) ABSTRACT

The present invention aims to provide a gas sensor that can favorably be assembled by proper positioning of a connection terminal relative to a separator and a subassembly unit for such a gas sensor. In an oxygen sensor, a separator has protruding portions formed on a surface of a front end part thereof; an outer connection terminal has an outer fitting portion fixed to outer circumferential surfaces of the protruding portions under its biasing force; and an inner connection terminal has an inner fitting portion fixed to inner circumferential surfaces of the protruding portions under its biasing force. Thus, it is less likely that the outer and inner connection terminals will be displaced in position relative to the separator and is possible to allow proper positioning of the outer and inner connection terminals.

14 Claims, 13 Drawing Sheets (a)

(b)

(a)

(b)

(c)

GAS SENSOR AND SUBASSEMBLY UNIT THEREFOR

CROSS REFERENCE TO RELATED APPLICATIONS

This application is a National Stage of International Application No. PCT/JP2012/000146 filed Jan. 12, 2012, claiming priority based on Japanese Patent Application No. 2011-030748filed Feb. 16, 2011, the contents of all of which are incorporated herein by reference in their entirety.

TECHNICAL FIELD

The present invention relates to a gas sensor having a cylindrical sensor element, a connection terminal fitted to the sensor element and a separator formed with a through hole in which a part of the connection terminal is inserted and a subassembly unit therefor.

BACKGROUND ART

As an example of a sensor having a sensor element to detect a gas under measurement, conventionally known is an oxygen sensor for measuring the concentration of oxygen in an automotive exhaust gas. There is known a sensor element for use in such an oxygen sensor, including a bottomed cylindrical solid electrolyte body, an inner electrode formed on an inner side of the solid electrolyte body and an outer electrode formed on an outer side of the solid electrolyte body, as disclosed in Patent Documents 1 and 2.

An inner connection terminal is fitted into a rear end portion of the sensor element and electrically connected to the inner electrode (of the sensor element). A sensor output lead is connected to a rear end portion of the inner connection terminal. In the case where a rod-shaped ceramic heater is inserted in the sensor element, the inner connection terminal is attached around the ceramic heater.

An outer connection terminal (ground connection terminal) is fitted onto the rear end portion of the sensor element and electrically connected to the outer electrode (of the sensor element). A ground lead is connected to a rear end portion of the outer connection terminal.

As shown in FIG. 13(a), the outer connection terminal P1 generally includes a cylindrical outer fitting portion P2 (having left and right wing sections) for contact with the sensor element from outside and an elongated extension portion P3 extending axially from a rear end (in the drawing, an upper end) of the outer fitting portion P2 (for connection with the lead).

On the other hand, the inner connection terminal P4 includes a cylindrical inner fitting portion P5 (having left and right wing sections) for contact with the sensor element from inside and an elongated extension portion P6 extending axially from a rear end of the inner fitting portion P5 (for connection with the lead) as shown in FIG. 13(b).

As shown in FIG. 13(c), a cylindrical separator P7 is provided with axial through holes P8 and P9 such that the extension portion P3 of the outer connection terminal P1 and the extension portion P6 of the inner connection terminal P4 are inserted and pass the through holes P8 and P9, respectively.

PRIOR ART DOCUMENTS

Patent Documents

Patent Document 1: Japanese Laid-Open Patent Publication No. 2007-285769

Patent Document 2: Japanese Laid-Open Patent Publication No. 2008-286731

SUMMARY OF THE INVENTION

Problems to be Solved by the Invention

The above-mentioned oxygen sensor is manufactured by inserting the extension portion P3 of the outer connection terminal P1 and the extension portion P6 of the inner connection terminal P4 into the respective through holes P8 and P9 of the separator P7. It is thus necessary to set the dimensions of the through holes P8 and P9 with some degree of margin in view of ease of insertion.

When the dimensions of the through holes P8 and P9 are set with some margin as shown in FIG. 13(d), the accurate positioning of the outer and inner connection terminals P1 and P4 is difficult due to the presence of a slight play circumferentially around the outer and inner connection terminals P1 and P4.

Further, the outer and inner connection terminals P1 and P4 may be slightly radially displaced (toward the inside or outside) relative to the center axis as shown in FIG. 13(e) when the dimensions of the through holes P8 and P9 are set with some margin. This also makes the positioning of the outer and inner connection terminals P1 and P4 difficult.

In recent years, it is common practice to assemble the oxygen sensor by combining the outer and inner connection terminals P1 and P4 and the separator P7 into one unit (called "subassembly unit") upon insertion of the extension portion P3 of the outer connection terminal P1 and the extension portion P6 of the inner connection terminal P4 into the through holes P8 and P9 of the separator P7, and then, fitting the outer fitting portion P2 of the outer connection terminal P1 and the inner fitting portion P5 of the inner connection terminal P4 to the sensor element by means of an automechanism.

If the outer and inner connection terminals P1 and P4 are not accurately positioned, there occur problems such as crushing of the outer fitting portion P2 of the outer connection terminal P1 and the inner fitting portion P5 of the inner connection terminal P4 at the time of fitting of the outer and inner connection terminals P1 and P4 to the sensor element so that the sensor assembling operation cannot be performed favorably.

The present invention has been made in order to solve the above problems. It is accordingly an object of the present invention to provide a gas sensor that can favorably be assembled by proper positioning of a connection terminal relative to a separator. It is also an object of the present invention to provide a subassembly unit for such a gas sensor.

Means for Solving the Problems (1) According to a first aspect of the present invention, there is provided a gas sensor subassembly unit for use in manufacturing a gas sensor, the gas sensor comprising: a cylindrical sensor element located on a front end side of the gas sensor; a connection terminal located on a rear end side of the sensor element and held in contact with an electrode of the sensor element; and a separator located rear of the sensor element and having a through hole in which a rear end part of the connection terminal is inserted, wherein the gas sensor subassembly unit comprises the connection terminal and the separator integrally mounted together; wherein the connection terminal has a cylindrical fitting portion formed on a front end part thereof so as to be fitted to the sensor element and brought into contact with the electrode of the sensor element and an extension portion formed on a rear end part thereof so as to extend rearward from the fitting portion and be inserted in the through hole of the separator; wherein the separator has a protruding portion formed on a surface of a front end part thereof so as to protrude frontward; and wherein the fitting portion of the connection terminal is fixed to a radially lateral surface of the protruding portion under the action of a biasing force of the fitting portion.

In the first aspect of the present invention, the protruding portion is formed on the surface of the front end part of the separator; and the fitting portion of the connection terminal is fixed to the radially lateral surface of the protrusion portion under its biasing force.

This makes it less likely that the connection terminal will be displaced in position relative to the separator as compared to conventional ones and thus enables proper positioning of the connection terminal relative to the separator. Because of such proper positioning of the connection terminal, it is possible to fit the connection terminal to the sensor element assuredly in the case of manufacturing (assembling) the gas sensor by means of e.g. an automechanism with the use of the subassembly unit in which the connection terminal is integrally mounted in the separator.

Herein, the expression "the fitting portion of the connection terminal is fixed to the radially lateral surface of the protruding portion" refers to not only a case where the fitting portion is in contact with and is fixed to the whole of the lateral surface of the protruding portion but also a case where the fitting portion is in contact with and is fixed to a part of the lateral surface of the protruding portion. It means that the lateral surface of the protruding portion may be inclined toward the (radially) outside or inside with respect to the axial direction of the gas sensor and thereby only partially contact with the fitting portion.

(2) According to a second aspect of the present invention, the gas sensor subassembly unit is characterized in that one or two or more protruding portions are formed on the surface of the front end part of the separator.

(3) According to a third aspect of the present invention, the gas sensor subassembly unit is characterized in that the connection terminal is adapted to be fitted onto the sensor element (that is, the connection terminal is adapted as an outer connection terminal) in such a manner as to satisfy the condition: an inner diameter of the fitting portion of the connection terminal (before fixed to the protruding portion)<an outer diameter of the protruding portion<an outer diameter of the sensor element.

(4) According to a fourth aspect of the present invention, the gas sensor subassembly unit is characterized in that the connection terminal is adapted to be fitted into the sensor element (that is, the connection terminal is adapted as an inner connection terminal) in such a manner as to satisfy the condition: an inner diameter of the sensor element<an inner diameter of the protruding portion<an outer diameter of the fitting portion of the connection terminal (before fixed to the protruding portion).

(5) According to a fifth aspect of the present invention, the gas sensor subassembly unit is characterized in that a cut is formed axially in the fitting portion of the connection terminal such that the fitting portion is divided into circumferentially opposite sections by the cut.

In this case, the fitting portion of the connection terminal can be formed into a substantially C-like curved shape, a partially open polygonal shape such as triangle shape or rectangle shape, or the like, when viewed in the axial direction.

(6) According to a sixth aspect of the present invention, the gas sensor subassembly unit is characterized in that the separator has a rotation preventing portion protruding frontward from the surface of the front end part thereof at a position along a rotational direction of the fitting portion of the connection terminal so as to prevent rotation of the fitting portion.

For example, the rotation preventing portion can be formed at a circumferentially distal end of the fitting portion adjacent to the cut.

(7) According to a seventh aspect of the present invention, there is provided a gas sensor comprising: a sensor element; and the gas sensor subassembly unit according to any one of the first to sixth aspects, the fitting portion of the connection terminal of the gas sensor subassembly unit being fitted to the sensor element.

Effects of the Invention

It is possible according to the first aspect of the present invention to not only allow easy mounting of the subassembly unit but also to prevent the fitting portion of the connection terminal from being crushed (due to positional displacement of the connection terminal) during the mounting and thereby limit the occurrence of defectives due to improper fitting.

In the second aspect of the present invention, the configuration of the protruding portion is exemplified. In the case of providing one protruding portion, it is possible to form the protruding portion with advantages such as simple configuration and toughness. In the case of providing a plurality of protruding portions, it is possible to form the required number of protruding portions separately at their desired positions according to the shape (in particular, complicated shape) of the fitting portion of the connection terminal and the shape of the surface of the front end part of the separator (such as the positions of the through hole and the insertion hole). In other words, the protruding portion can be easily provided so as to comply with the various shapes of the fitting portion and the separator.

In the third aspect of the present invention, the inner diameter of the fitting portion is made smaller than the outer diameter of the protruding portion. This makes it possible that, when the fitting portion of the connection terminal is put onto the protruding portion, the fitting portion can be fixed to the outer circumferential surface of the protruding portion under the own (inward) biasing force caused by expansion of the fitting portion. Further, the outer diameter of the sensor element is made larger than the outer diameter of the protruding portion. This makes it possible that, when the fitting portion is fitted onto the sensor element, the fitting portion can be released from being fixed by the protruding portion upon expansion of the fitting portion and thereby can be put over the sensor element.

In the fourth aspect of the present invention, the inner diameter of the protruding portion is made smaller than the outer diameter of the fitting portion. This makes it possible that, when the fitting portion of the connection terminal is put into the protruding portion, the fitting portion can be fixed to the inner circumferential surface of the protruding portion under the own (outward) biasing force caused by contraction of the fitting portion. Further, the inner diameter of the sensor element is made smaller than the inner diameter of the protruding portion. This makes it possible that, when the fitting portion is fitted into the sensor element, the fitting portion can be released from being fixed by the protruding portion upon contraction of the fitting portion and thereby can be put into the sensor element.

In the fifth aspect of the present invention, the cylindrical fitting portion is circumferentially divided (when viewed in the axial direction) so as to form the circumferentially opposite cantilever wing sections. This makes it possible to secure the sufficient elasticity of the fitting portion for fitting to the sensor element. The connection terminal can be easily formed into such a shape by cutting and bending a single metal plate.

In the sixth aspect of the present invention, the rotation preventing portion is provided on the surface of the front end part of the separator. This makes it possible to prevent rotation of the connection terminal (e.g. in the circumferential direction).

In the manufacturing of the gas sensor according to the seventh embodiment of the present invention, the connection terminal can be assuredly fitted to the sensor element by proper positioning of the connection terminal as mentioned above. It is thus possible to limit the occurrence of defectives (due to improper fitting caused by positional displacement of the connection terminal) while allowing easy mounting of the subassembly unit.

DESCRIPTION OF THE EMBODIMENTS

Hereinafter, exemplary embodiments of the present invention will be described below with reference to the drawings.
First Embodiment The present first embodiment specifically refers to, as an example of a gas sensor, an oxygen sensor for measuring the concentration of oxygen in an exhaust gas of an automotive vehicle.

The oxygen sensor of the present embodiment will be first described below with reference to FIGS. 1 and 2. It is herein noted that: the lower and upper sides in FIGS. 1 and 2 correspond to the front and rear sides of the oxygen sensor, respectively.

Figure 1:
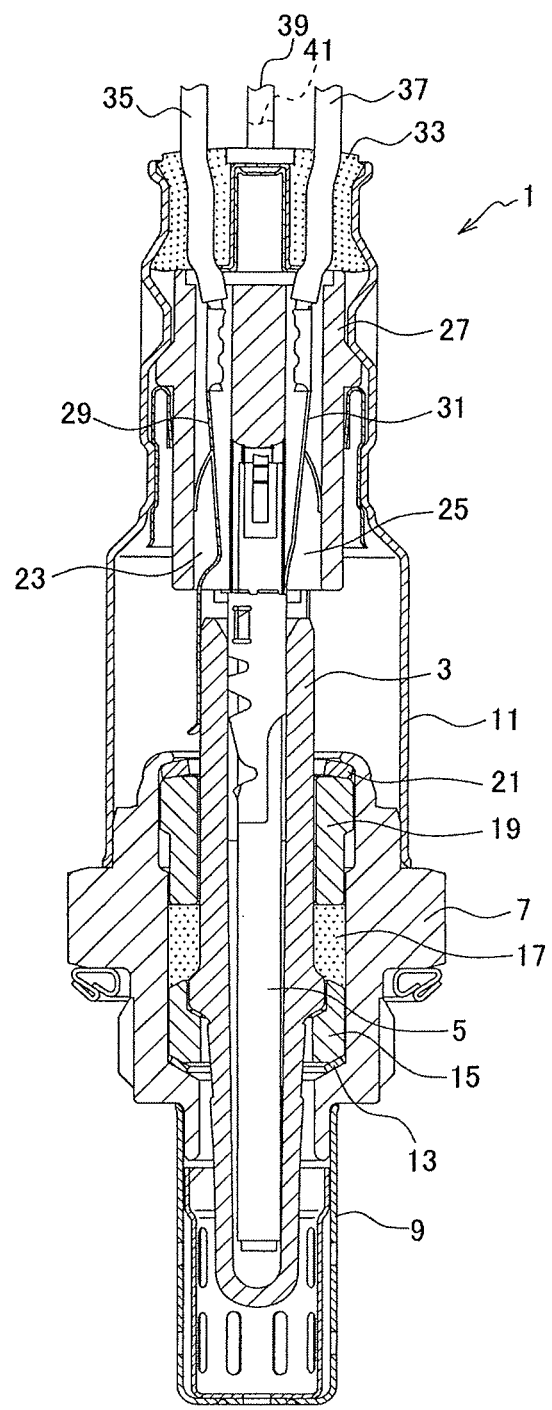
FIG. 1 is an axially cutaway view of an oxygen sensor according to a first embodiment of the present invention.

Referring to FIG. 1, the oxygen sensor 1 of the present embodiment includes a narrow cylindrical sensor element 3 having a closed front end, a cylindrical column-shaped ceramic heater 5 inserted in the sensor element 3, a cylindrical metal shell 7 in which the sensor element 3 is inserted and fixed, a cylindrical metallic protector 9 coaxially fixed to a front end portion of the metal shell 7 and a cylindrical metallic outer tube 11 coaxially fixed to a rear end portion of the metal shell 7. Herein, the ceramic heater 5 is equipped with, for example, an alumina body and a heating resistor.

For fixing and gas sealing of the sensor element 3, a metallic packing 13, a ceramic supporting member 15, a filling member 17 of talc powder, a ceramic sleeve 19 and a metallic gasket 21 are arranged between the sensor element 3 and the metal shell 7 in this order from the front side.

A ceramic separator 27 with a plurality of through holes 23 and 25 is arranged on a rear end portion of the sensor element 3. Metallic outer and inner connection terminals 29 and 31 are inserted in the through holes 23 and 25, respectively, for electrical connection to the sensor element 3. A grommet 33 of fluorocarbon resin is sealed in a rear end of the outer tube 11. Leads 35, 37, 39 and 41 are passed through the grommet 33. The leads 35 and 37 are connected to the outer and inner connection terminals 29 and 31, whereas the leads 39 and 41 are connected to the ceramic heater 5.

These leads 35 to 41 are also electrically connected to a sensor control unit and an electrical control unit (ECU) of the automotive vehicle, both of which are situated apart from the oxygen sensor 1, although not shown in the drawings.

Hereinafter, the main sensor structural components will be described below in more detail.

Figure 2:
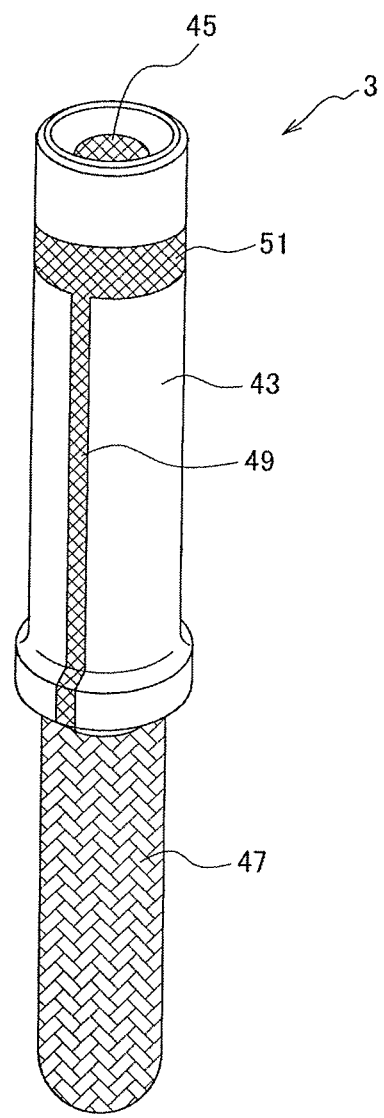
FIG. 2 is a perspective view of a sensor element of the oxygen sensor.

As shown in FIG. 2, the sensor element 3 has a bottomed cylindrical base body 43 formed of solid electrolyte containing zirconia as a main constituent. A porous inner electrode (reference electrode) 45 is formed of Pt or Pt alloy on substantially the whole of an inner circumferential surface of the base body 43. The inner connection terminal 31 is brought in contact with the inner electrode 45.

On the other hand, a porous outer electrode (detection electrode) 47 is formed of Pt or Pt alloy on a front end part of an outer circumferential surface of the base body 43 such that the whole of the front end part of the outer circumferential surface of the base body 43 is covered with the outer electrode 47. An electrode lead portion 49 is formed so as to extend rearward from the outer electrode 47. An annular electrode portion 51 is formed so as to be connected with the electrode lead portion 49. The outer connection terminal 29 is brought into contact with the annular electrode portion 51. Further, a porous electrode protection layer of heat-resistant ceramic material (not shown) is formed on a surface of the outer electrode 47 so as to protect the outer electrode 47 from poisoning by the exhaust gas.

As shown in FIG. 3(a), the outer connection terminal 29 is an elongated ground terminal having a lower end part fitted onto the sensor element 3 and held in contact with the annular electrode portion 51 and an upper end part connected to the lead 35.

More specifically, the outer connection terminal 29 is formed by bending one metal plate of e.g. Inconel and includes an elastic cylindrical outer fitting portion 53 located on a lower end side thereof and an extension portion 55 extending axially upwardly from an upper end side of the outer fitting portion 53.

The outer fitting portion 53 has a pair of left and right wing sections 57 and 59 curved into arc shapes (when viewed in an axial direction thereof). A gap (slit) 61 is provided between circumferentially distal ends of the left and right wing sections 57 and 59 (in a direction circling the center axis) so that the left and right wing sections 57 and 59 are axially separated from each other by the gap 61.

A plurality of substantially evenly spaced guide pieces 63 are formed on a lower end of the outer fitting portion 53 so as to protrude diagonally outwardly (in a direction going away from the center axis) and guide easy fitting of the outer connection terminal 29 onto an upper end of the sensor element 3.

The extension portion 55 has a bottom section 65 extending inwardly upwardly from the outer fitting portion 53 (more specifically, from a base end part of the left and right wing sections 57 and 59), an intermediate section 67 extending axially upwardly from the bottom section 65 and a holding section 69 located upward of the intermediate section 67 and adapted to hold therein the lead 35. A protrusion piece 71 is formed on the intermediate section 67 so as to protrude outwardly.

As shown in FIG. 3(b), the inner connection terminal 31 is a terminal formed from one metal plate of e.g. Inconel and having a cylindrical inner fitting portion 73 located on a front end side thereof and fitted into the sensor element 3 (around the ceramic heater 5) and an elongated extension portion 75 extending axially from a rear end of the inner fitting portion 73.

The inner fitting portion 73 has a pair of left and right wing sections 77 and 79 curved into arc shapes (when viewed in an axial direction thereof). A gap 81 is provided between circumferentially distal ends of the left and right wing sections 77 and 79 so that the left and right wing sections 77 and 79 are axially separated from each other by the gap 81.

The extension portion 75 has a bottom section 83 extending outwardly upwardly from the inner fitting portion 73, an intermediate section 85 extending axially upwardly from the bottom section 83 and a holding section 87 located upward of the intermediate section 85 and adapted to hold therein the lead 37. A protrusion piece 89 is formed on the intermediate section 85 so as to protrude outwardly.

Figure 4:
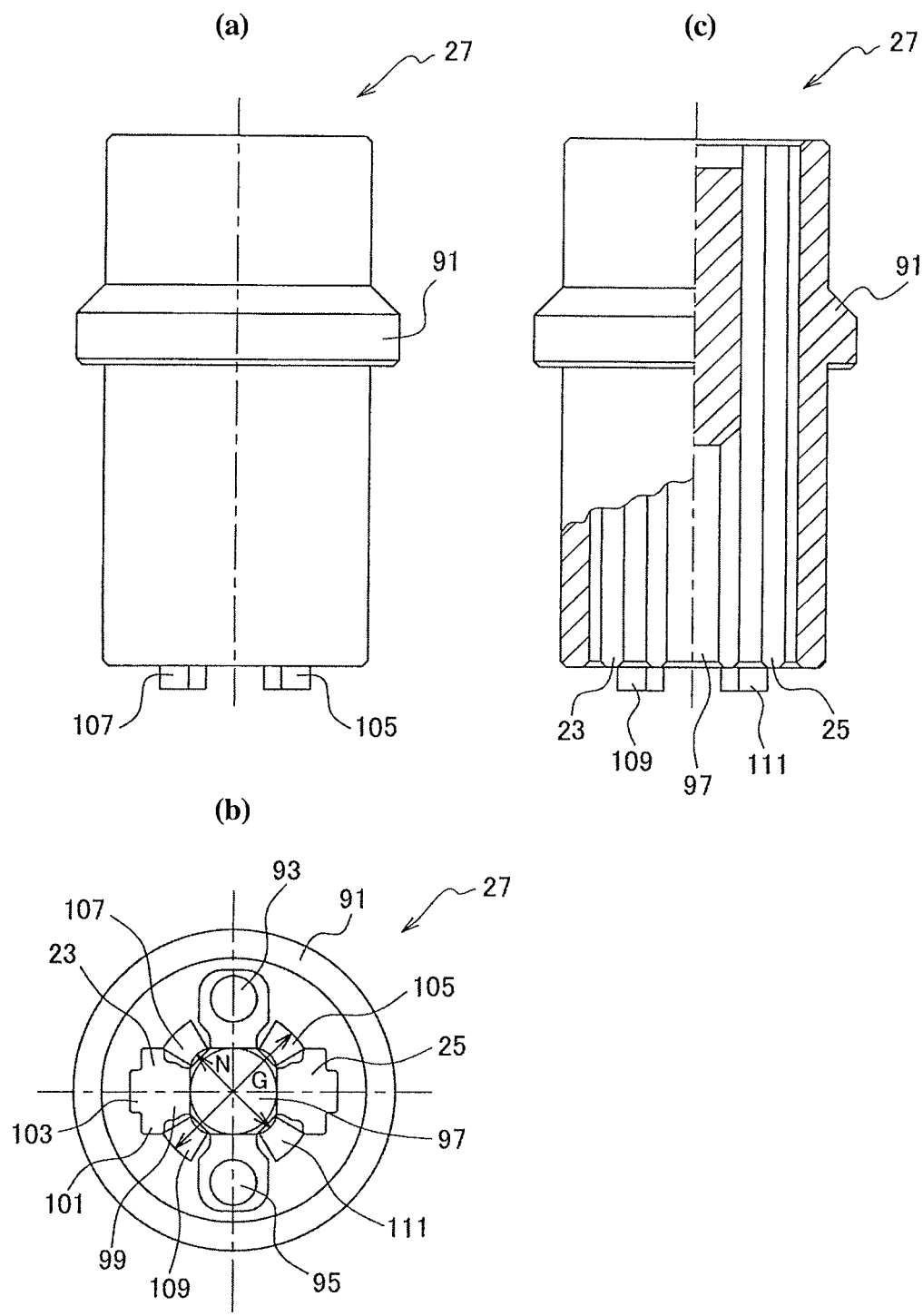
FIG. 4(a) is a front view of a separator of the oxygen sensor.
FIG. 4(b) is a plan view of a front end part of the separator.
FIG. 4(c) is a partially cutaway view of the separator.

As shown in FIG. 4, the separator 27 is a cylindrical member of electrically insulating alumina and has a flange portion 91 formed on an outer circumferential surface thereof, a pair of through holes 23 and 25 formed axially and symmetrically with respect to the axis center, another pair of through holes 93 and 95 formed axially and symmetrically with respect to the axis center (aligned perpendicular to the direction of arrangement of the through holes 23 and 25) and an elongated insertion hole 97 formed (with a closed rear end) along the axis center.

The through hole 23 is adapted to allow insertion of the extension portion 55 of the outer fitting terminal 29 therein.

As shown in FIG. 4(b), the through hole 23 includes a center hole region 99 having a substantially trapezoidal cross-section in a direction perpendicular to the axial direction, a slit region 101 extending in a slit-like manner from the center hole region 99 vertically in the drawing and a protruding hole region 103 protruding outwardly from the center hole region 99.

As will be explained later, the through hole 23 is so configured that the widened intermediate section 67 of the extension portion 55 is fitted in the slit region 101 with the protrusion piece 71 engaged in the protruding hole region 103. The other through hole 25 is also formed into the same shape.

In the present embodiment, the separator 27 has four protruding portions (first to fourth protruding portions) 105 to 111 protruding from a surface of a front end part thereof. More specifically, the protruding portions 105 to 111 are arranged at circumferentially evenly spaced positions between the through holes 23, 25, 93 and 95 about the center axis and each formed into a cylindrical column protrusion. Each of the protruding portions 105 to 111 has an inner circumferential surface shaped with an inner diameter of a circle N and an outer circumferential surface shaped with an outer diameter of a circle G when viewed in plan.

Figure 5:
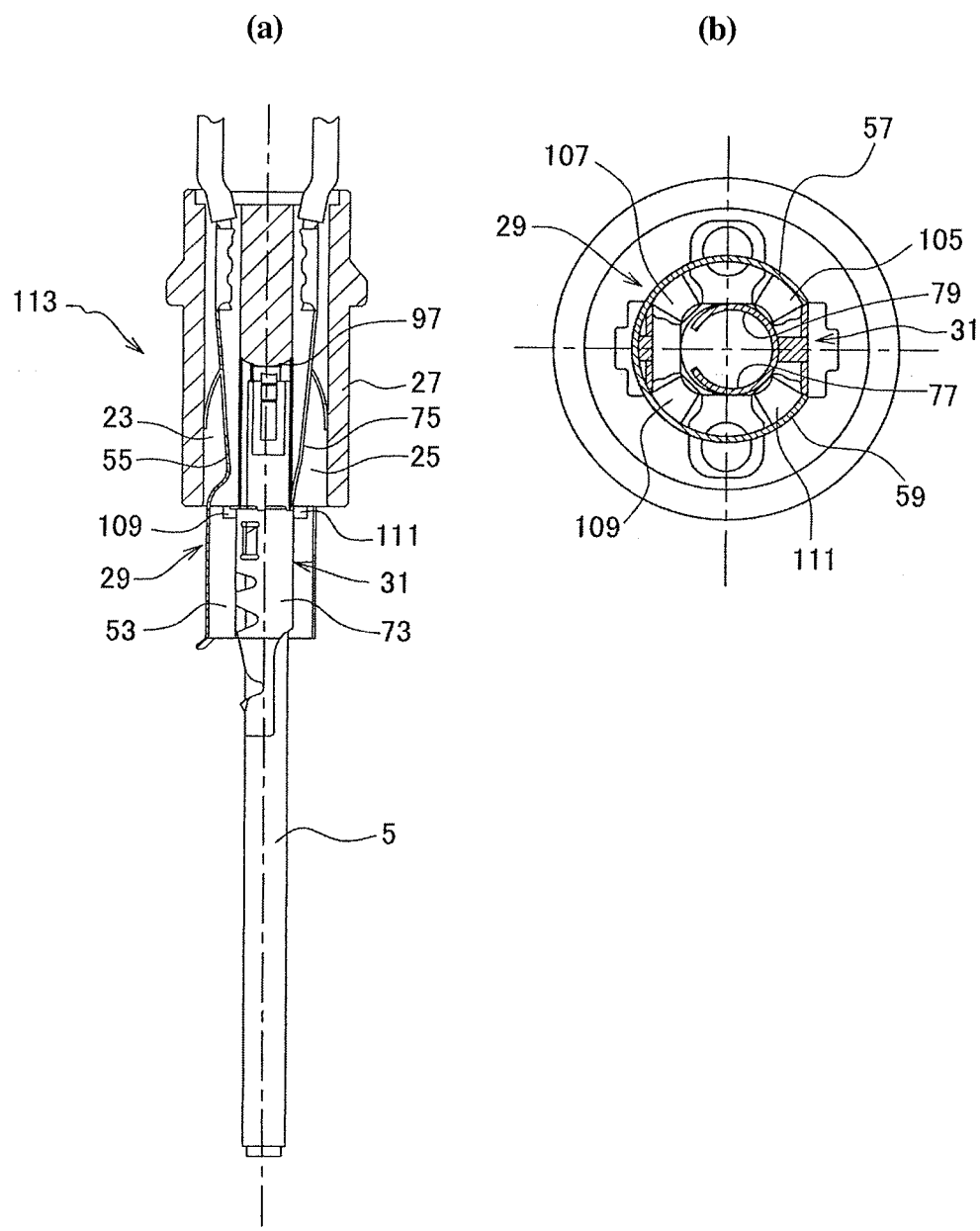
FIG. 5(a) is a cutaway view of a subassembly unit for the oxygen sensor.
FIG. 5(b) is a schematic enlarged view showing the arrangement of the outer and inner connection terminals in the front end part of the separator.

Herein, a state (subassembly unit 113) in which the outer and inner connection terminals 29 and 31 are mounted to the separator 27 is shown by enlargement in FIG. 5(a).

In this state, the outer fitting portion 53 of the outer connection terminal 29 is arranged on the lower end of the separator 27; and the extension portion 55 of the outer connection terminal 29 is inserted in the through hole 23 of the separator 27 as shown in the drawing. Similarly, the inner fitting portion 73 of the inner connection terminal 31 is arranged on the lower end of the separator 27; and the extension portion 75 of the inner connection terminal 31 is inserted in the through hole 25 of the separator 27.

The inner fitting portion 73 of the inner connection terminal 31 is also integrally fitted around the rear end portion of the ceramic heater 5. The rear end portion of the ceramic heater 5 is inserted in the insertion hole 97 of the separator 27.

In the present embodiment, the left and right wing sections 57 and 59 of the outer connection terminal 29 are fitted onto radially outward lateral surfaces (outer circumferential surfaces) of the protruding portions 105 to 111 and fixed in position under the action of its own elasticity (upon expansion of these wing sections by the outer circumferential surfaces of the protruding portions 105 to 111) so as not to move circumferentially and radially.

The left and right wing sections 77 and 79 of the inner connection terminal 31 are fitted into radially inward lateral surfaces (inner circumferential surfaces) of the protruding portions 105 to 111 and fixed in position under the action of its own elasticity (upon contraction of these wing sections by the inner circumferential surfaces of the protruding portions 105 to 111) so as not to move circumferentially and radially.

Further, the dimensions of the respective components are set so as to satisfy the following condition (1) in the present embodiment: the inner diameter of the outer fitting portion of the outer connection terminal (before fixed to the protruding portions) <the outer diameter of the protruding portions <the outer diameter of the sensor element (1). In this configuration, the outer connection terminal 29 is fitted on and fixed in position to the outer circumferential surfaces of the protruding portions 105 to 111 of the separator 27 before the assembling of the oxygen sensor 1 and is widened in diameter upon fitting of the outer connection terminal 29 onto the sensor element 3 and thereby released from being fixed by the protruding portions 105 to 111 during the assembling of the oxygen sensor 1 as will be explained later.

Figure 6:
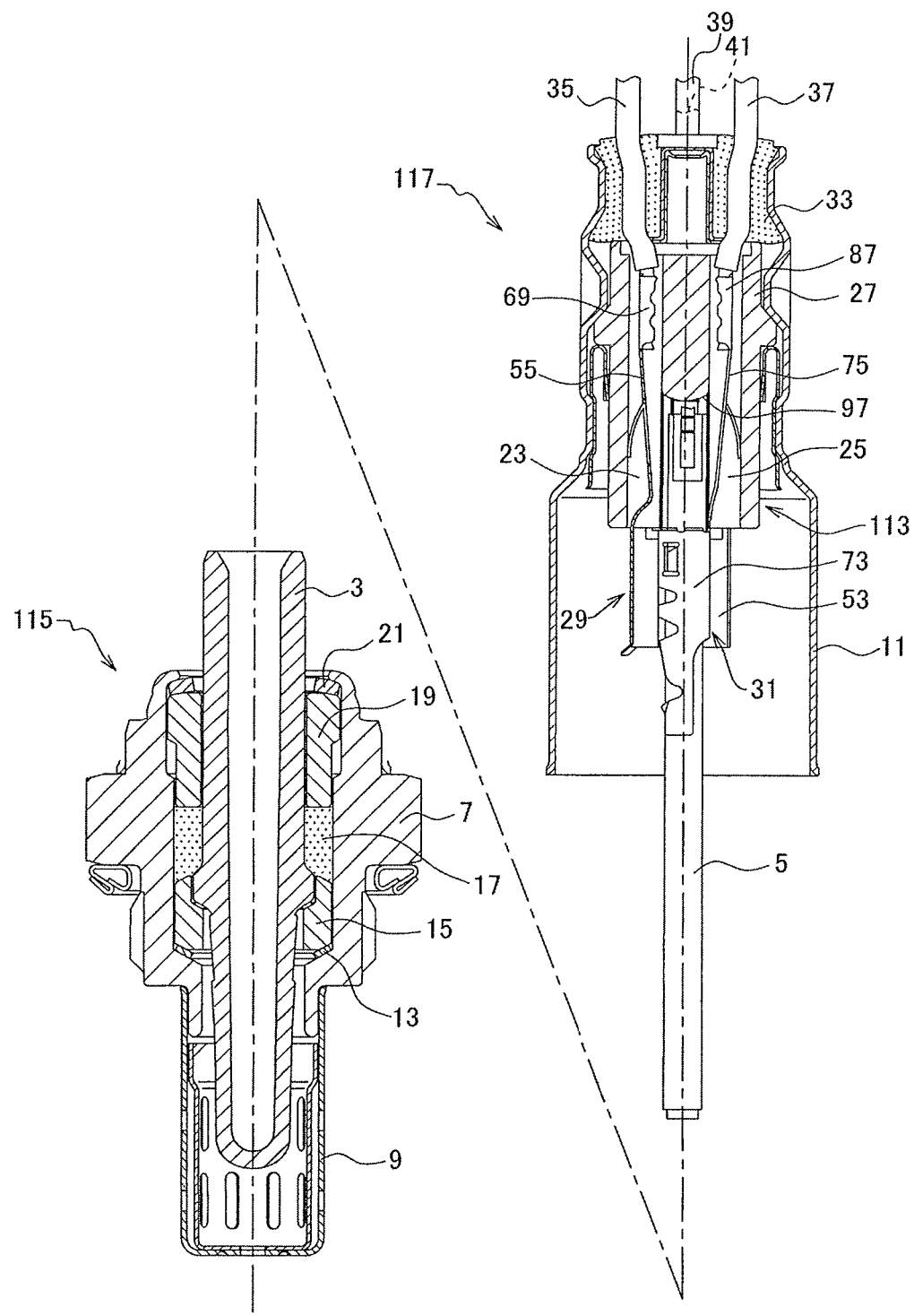
FIG. 6 is a schematic view showing a state in which the oxygen sensor is separated into two subassemblies.

The dimensions of the respective components are also set so as to satisfy the following condition (2) in the present embodiment: the inner diameter of the sensor element <the inner diameter of the protruding portions <the outer diameter of the inner fitting portion of the inner connection terminal (before fixed to the protruding portions) (2). In this configuration, the inner connection terminal 31 is fitted in and fixed in position to the inner circumferential surfaces of the protruding portions 105 to 111 of the separator 27 before the assembling of the oxygen sensor 1 and is narrowed in diameter upon fitting of the inner connection terminal 31 into the sensor element 3 and thereby released from being fixed by the protruding portions 105 to 111 during the assembling of the oxygen sensor 1 as will be explained later.

b) Next, a manufacturing method of the oxygen sensor 1 of the present embodiment will be described below with reference to FIGS. 6 and 7. FIG. 6 shows the state after crimping of the grommet 33 and the like.

First, a front subassembly module 115 is provided by joining the protector 9 to the front end portion of the metal shell 7 and fixing the sensor element 3 into the metal shell 7 by crimping, with the packing 13, the supporting member 15, the filling member 17, the sleeve 19 and the gasket 21 interposed therebetween, as shown in FIG. 6.

Figure 3:
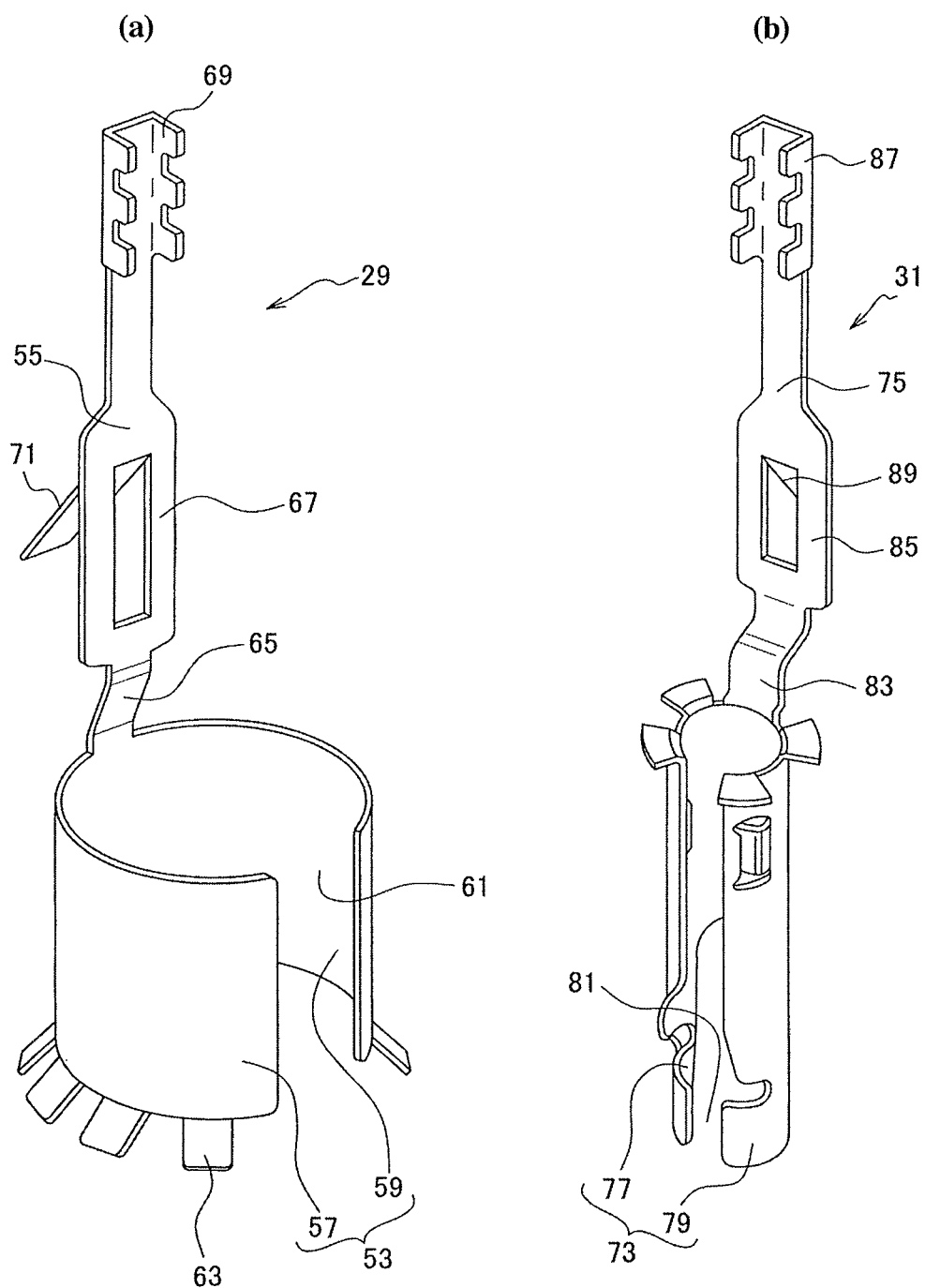
FIG. 3(a) is a perspective view of an outer connection terminal of the oxygen sensor.
FIG. 3(b) is a perspective view of an inner connection terminal of the oxygen sensor.

On the other hand, each of the outer and inner connection terminals 29 and 31 is shaped as shown in FIG. 3 by stamping the conductive plate material. After that, core wires of the leads 35 and 37 are fixed by crimping to the holding sections 69 and 87 of the outer and inner connection terminals 29 and 31, respectively, as shown in FIG. 6. The inner connection terminal 31 and the ceramic heater 5 are combined into one by fitting the inner fitting portion 73 of the inner connection terminal 31 on the rear end portion of the ceramic heater 5. Further, the leads 39 and 41 are connected to the ceramic heater 5.

The subassembly unit 113 is subsequently produced by mounting the outer and inner connection terminals 29 and 31 and the ceramic heater 5 into the separator 27.

More specifically, the outer and inner connection terminals 29 and 31 and the ceramic heater 5 are mounted into the separator 27 by inserting the extension portions 55 and 75 of the outer and inner connection terminals 29 and 31 and the rear end portion of the ceramic heater 5 (to which the leads 39 and 41 are connected) in the through holes 23 and 25 and the insertion hole 97 of the separator 27, respectively, and pulling the rear end portions of these respective components into the separator 27.

A rear subassembly module 117 is then provided by inserting the separator 27 in the outer tube 11, passing the leads 35 to 41 through the grommet 33 and fitting the grommet 33 in the rear end of the outer tube 11.

As explained above, the front subassembly module 115 in which the sensor element 3 and the like are retained in the metal shell 7 and the rear subassembly module 117 in which the outer and inner connection terminals 29 and 31, the ceramic heater 5 and the like are retained in the outer tube 11 are produced by the separate process steps.

The thus-obtained subassembly modules 115 and 117 are assembled together in such a manner that the axial direction of the subassembly module 115 agrees with the axial direction of the subassembly module 117. In the actual assembling process, the rear subassembly module 117 is placed below the front subassembly module 115 in contrast to FIG. 6 so that the front subassembly module 115 is attached from above to the rear subassembly module 117 by means of an automechanism.

Figure 7:
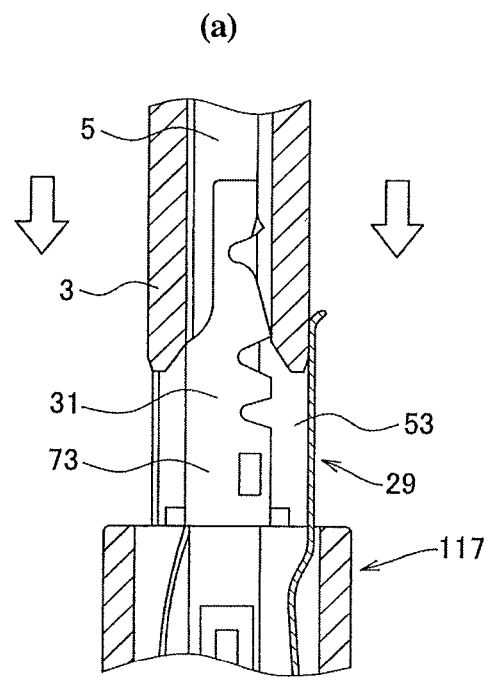
FIG. 7 is a schematic view showing how the oxygen sensor is assembled from the two subassemblies.
Figure 7:
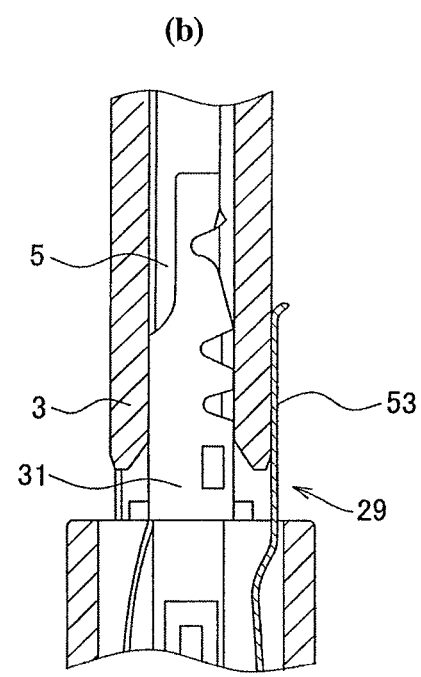

More specifically, the rear subassembly module 117 is fixed to an assembling device, with the ceramic heater 5 facing upward, as shown in FIG. 7. The front subassembly module 115 is held above the rear subassembly module 117, and then, pressed down from above to a given fixed position in the rear subassembly module 117 by inserting the ceramic heater 5 into the sensor element 3, fitting the inner fitting portion 73 of the inner connection terminal 31 into the sensor element 3 and fitting the outer fitting portion 53 of the outer connection terminal 29 onto the rear end portion of the sensor element 3.

Simultaneously with the above pressing operation, the front end portion of the outer tube 11 is fitted and crimped onto the rear end portion of the metal shell 7. Further, a part of the outer tube 11 corresponding in position to a center portion of the separator 27 and the grommet 13 is crimped. The fitted front end portion of the outer tube 11 is then subjected to laser welding. In this way, the oxygen sensor 1 is completed by combining the front and rear subassembly modules 115 and 117 into one.

In the present embodiment, the dimensions of the respective components are set so as to satisfy the condition (1) as mentioned above. Thus, the outer connection terminal 29 is accurately fixed in position to the outer circumferential surfaces of the protruding portions 105 to 111 of the separator 29 before the assembling of the oxygen sensor 1, and then, is widened in diameter and released from being fixed by the protruding portions 105 to 111 upon fitting of the outer connection terminal 29 onto the sensor element 3 during the assembling of the oxygen sensor 1 from the subassembly modules 115 and 117.

Similarly, the dimensions of the respective components are set so as to satisfy the condition (2) as mentioned above in the present embodiment. Thus, the inner connection terminal 31 is accurately fixed in position to the inner circumferential surfaces of the protruding portions 105 to 111 of the separator 27 before the assembling of the oxygen sensor 1, and then, is narrowed in diameter and released from being fixed by the protruding portions 105 to 111 upon fitting of the inner connection terminal 31 into the sensor element 3 during the assembling of the oxygen sensor 1 from the subassembly modules 115 and 117.

c) As described above, the present embodiment is characterized in that: the frontward protruding portions 105 to 111 are formed on the surface of the front end part of the separator 27; and the outer and inner fitting portions 53 and 73 of the outer and inner connection terminals 29 and 31 are fixed to the outer and inner circumferential surfaces of the protruding portions 105 to 111 under biasing forces thereof, respectively.

This makes it less likely that the outer and inner connection terminals 29 and 31 will be displaced in position relative to the separator 27 in the subassembly unit 113 as compared to the conventional ones and thereby enables accurate positioning of the outer and inner connection terminals 29 and 31.

Due to such accurate positioning of the outer and inner connection terminals 29 and 31, the outer and inner connection terminals 29 and 31 can be fitted to the sensor element 3 assuredly without damage in the case of manufacturing the oxygen sensor 1 by means of an automechanism with the use of the subassembly unit 113 in which the outer and inner connection terminals 29 and 31 are mounted to the separator 27. It is therefore possible to not only allow easy mounting of the subassembly unit 113 but also to prevent the occurrence of defectives.

In addition, the four protruding portions 105 to 111 are formed separately and shaped to fit with the outer and inner fitting portions 53 and 73 of the outer and inner connection terminals 29 and 31 in the present embodiment. This allows adequate positioning of the outer and inner connection terminals 29 and 31 even when large protruding portions cannot be formed due to the shape of the front end part of the separator 27 (there is no space for such large protruding portions).

Second Embodiment

The second embodiment will be next described below. Herein, description of contents of the second embodiment similar to those of the first embodiment will be omitted herefrom.

As the present second embodiment is different from the first embodiment in the shape of the separator, the separator will be hereinafter explained below in detail.

Figure 8:
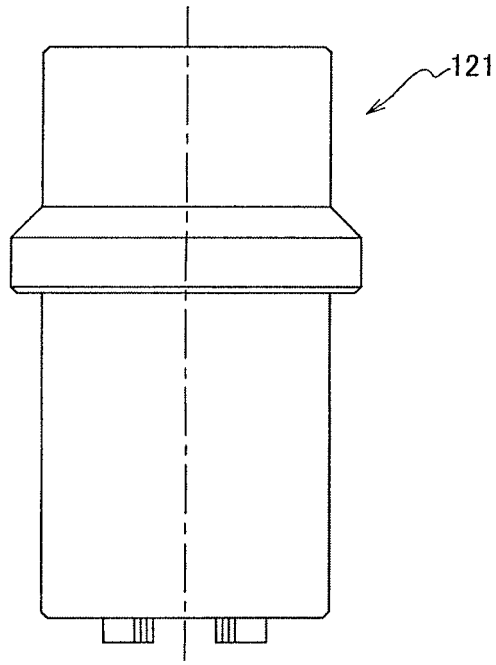
FIG. 8(a) is a front view of a separator of an oxygen sensor according to a second embodiment of the present invention.
FIG. 8(b) is a plan view of a front end part of the separator.
FIG. 8(c) is a schematic view showing the arrangement of an outer connection terminal and an inner connection terminal in the front end part of the separator.
Figure 8:
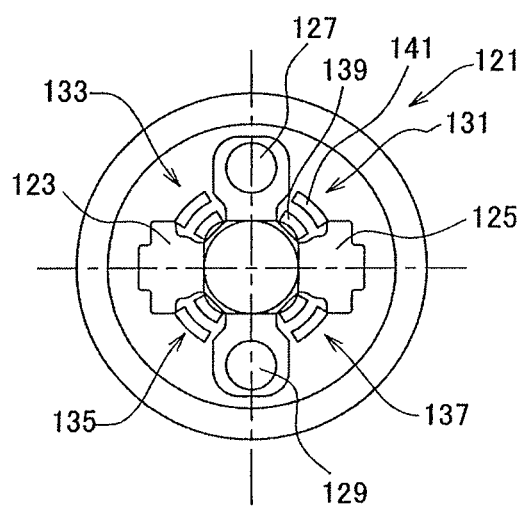
Figure 8:
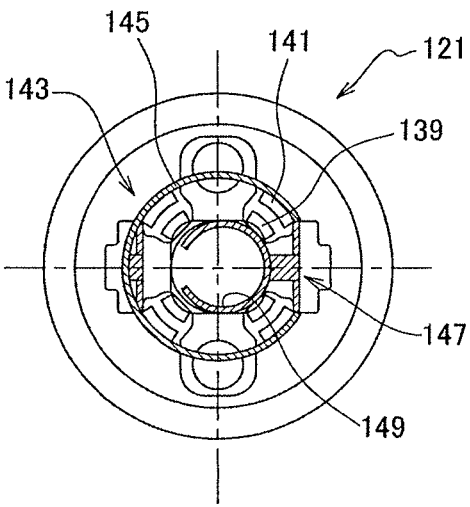

As shown in FIGS. 8(a) and (b), the separator 121 of the oxygen sensor is cylindrical in shape in the present embodiment as in the case of the first embodiment. Four through holes 123 to 129 are formed axially in the separator 121 (in the same manner as in the first embodiment).

Four protruding portions (first to fourth protruding portions) 131 to 137 are formed on the separator 121 at circumferentially evenly spaced positions between the through holes 123 to 129.

Differently from the first embodiment in which each protruding portion is formed as an integral structural member, each of the protruding portions 131 to 137 has two structural members such that the structural members of the protruding portions 131 to 137 are doubled concentrically about the center axis of the separator 121 when viewed in plan in the present embodiment. In other words, each of the protruding portions 131 to 137 has an arc-shaped inner wall 139 on a radially inner side thereof and an arc-shaped outer wall 141 located outward of the inner wall 139 with some arc-shaped space left therebetween.

The outer fitting portion 145 of the outer connection terminal 143 is fixed in position to the outer circumferential surfaces of the outer walls 141 of the protruding portions 131 to 137 under the action of its own elasticity as shown in FIG. 8(c).

Further, the inner fitting portion 149 of the inner connection terminal 147 is fixed in position to the inner circumferential surfaces of the inner walls 139 of the protruding portions 131 to 137 under the action of its own elasticity.

It is therefore possible in the present embodiment to obtain the same effects as in the first embodiment.

Third Embodiment

The third embodiment will be next described below. Herein, description of contents of the third embodiment similar to those of the first embodiment will be omitted herefrom.

As the present third embodiment is different from the first embodiment in the shape of the separator, the separator will be explained below in detail.

Figure 9:
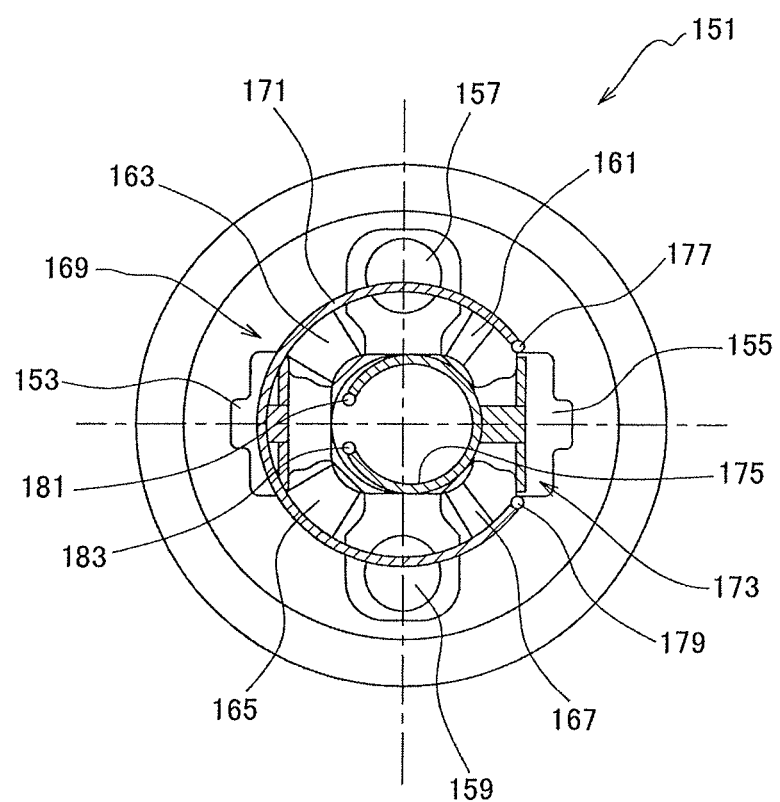
FIG. 9 is a schematic view showing the arrangement of an outer connection terminal and an inner connection terminal in a front end part of a separator of an oxygen sensor according to a third embodiment of the present invention.

As shown in FIG. 9, the separator 151 of the oxygen sensor is cylindrical in shape in the present embodiment as in the case of the first embodiment. Four through holes 153 to 159 are formed axially in the separator 151 (in the same manner as in the first embodiment).

Four protruding portions (first to fourth protruding portions) 161 to 167 are formed on the separator 151 at circumferentially evenly spaced positions between the through holes 153 to 159.

The outer fitting portion 171 of the outer connection terminal 169 is fixed in position to the outer circumferential surfaces of the protruding portions 161 to 167 under the action of its own elasticity.

Further, the inner fitting portion 175 of the inner connection terminal 173 is fixed in position to the inner circumferential surfaces of the protruding portions 161 to 167 under the action of its own elasticity.

In the present embodiment, rotation preventing portions 177 and 179 are formed on the surface of the front end part of the separator 151 (the front side of the drawing) at positions adjacent to circumferentially distal ends of the outer fitting portion 171 of the outer connection terminal 169 so as to prevent circumferential rotation of the outer connection terminal 169. When the outer fitting portion 171 receives a rotational force, the distal ends of the outer fitting portion 171 are brought into the rotation preventing portions 177 and 179, respectively.

Similarly, rotation preventing portions 181 and 183 are formed on the surface of the front end part of the separator 151 at positions adjacent to circumferentially distal ends of the inner fitting portion 175 of the inner connection terminal 173 so as to prevent circumferential rotation of the inner connection terminal 173. When the inner fitting portion 175 receives a rotational force, the distal ends of the inner fitting portion 175 are brought into contact with the rotation preventing portions 181 and 183, respectively.

The positions of the rotation preventing portions 177 to 183, when viewed in plan, are set so as not to interfere with deformations of the outer and inner fitting portions 171 and 175 of the outer and inner connection terminals 169 and 173 during the assembling of the oxygen sensor.

It is therefore possible in the present embodiment to obtain the same effects as in the first embodiment. It is also possible to secure the advantage of high positioning accuracy because the rotation preventing portions 177 to 183 are formed to prevent rotation of the outer and inner connection terminals 169 and 173 such that the outer and inner connection terminals 169 and 173 are less likely to be displaced in position in the present embodiment.

Fourth Embodiment

The fourth embodiment will be next described below. Herein, description of contents of the fourth embodiment similar to those of the first embodiment will be omitted herefrom.

The present fourth embodiment is obviously different from the first embodiment in that the oxygen sensor has no ceramic heater (i.e. the oxygen sensor has a heater-less structure).

Figure 10:
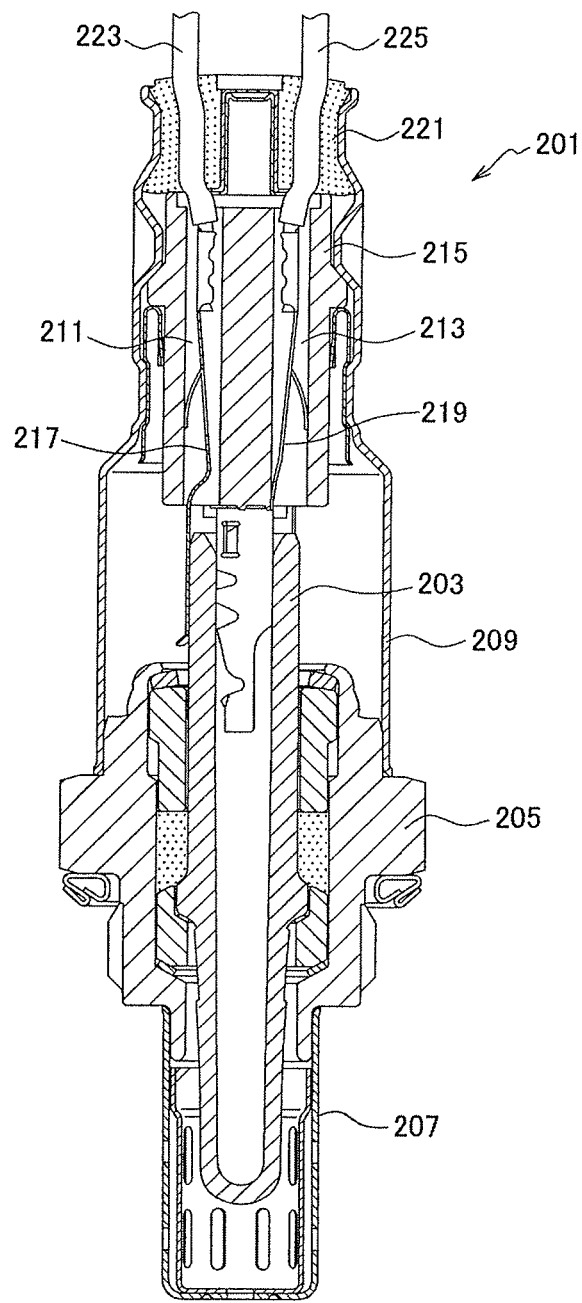
FIG. 10 is an axial cutaway view of an oxygen sensor according to a fourth embodiment of the present invention.

As shown in FIG. 10, the oxygen sensor 201 of the present embodiment includes a sensor element 203, a metal shell 205, a protector 207 and an outer tube 209 as in the case of the first embodiment.

A separator 215 with a pair of through holes 211 and 213 is arranged on a rear end portion of the sensor element 3. Outer and inner connection terminals 217 and 219 are inserted in the through holes 211 and 213, respectively, for electrical connection to the sensor element 3. A grommet 221 is sealed in a rear end of the outer tube 209. Leads 223 and 225 are passed through the grommet 221 and connected to the outer and inner connection terminals 217 and 219.

Figure 11:
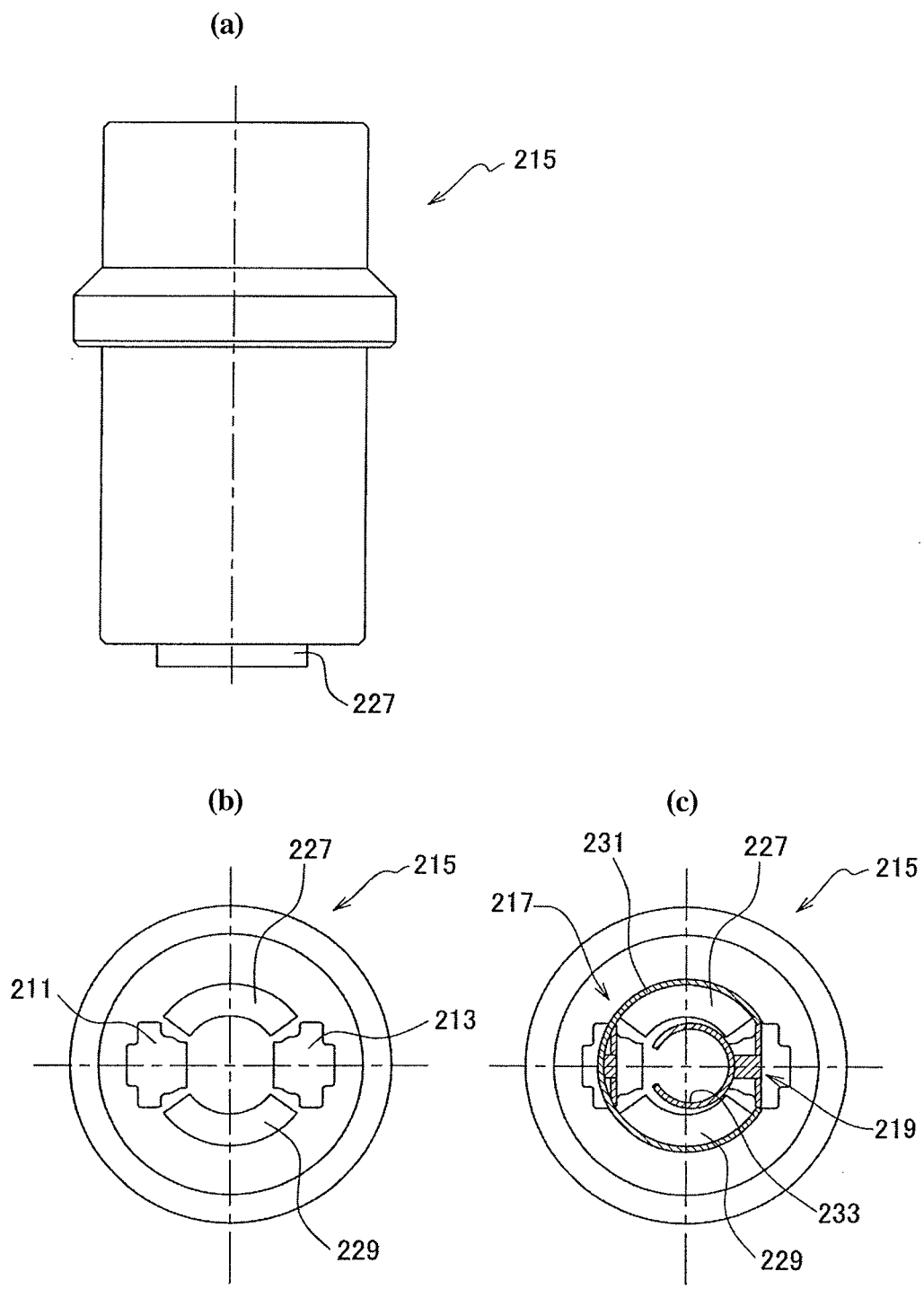
FIG. 11(a) is a front view of a separator of the oxygen sensor according to the fourth embodiment.
FIG. 11(b) is a plan view of a front end part of the separator.
FIG. 11(c) is a schematic view showing the arrangement of an outer connection terminal and an inner connection terminal in the front end part of the separator.

The separator 215 is of the type shown in FIGS. 11(a) and (b) as no ceramic heater is used in the present embodiment.

The separator 215 is cylindrical in shape as in the case of the first embodiment. The through holes 211 and 213 are formed axially in the separator 215 at two opposed positions. A pair of protruding portions (first and second protruding portions) 227 and 229 each having an arc shape (when viewed in plan) are formed on the separator 215 at opposed positions between the through holes 211 and 213. Outer and inner circumferential surfaces of the protruding portions 227 and 229 are arranged concentrically about the center axis of the separator 215 when viewed in plan.

As shown in FIG. 11(c), the outer fitting portion 231 of the outer connection terminal 217 is fixed in position to the outer circumferential surfaces of the protruding portions 227 and 229 under the action of its own elasticity in the present embodiment.

Further, the inner fitting portion 233 of the inner connection terminal 219 is fixed in position to the inner circumferential surfaces of the protruding portions 227 and 229 under the action of its own elasticity.

It is therefore possible in the present embodiment to obtain the same effects as in the first embodiment.

The present invention is not limited to the above-mentioned embodiments. Various changes and modifications can be made within the technical scope of the present invention.

Figure 12:
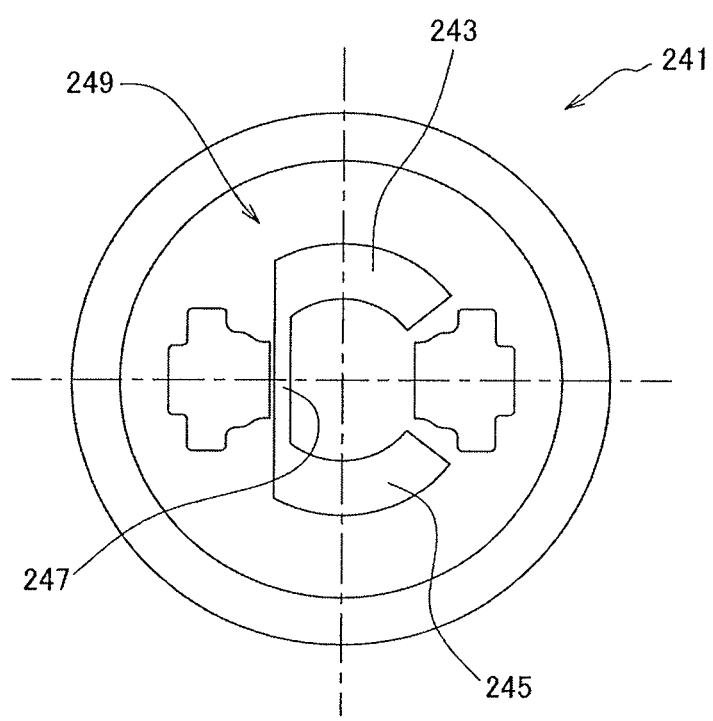
FIG. 12 is a plane view of a front end part of another separator.
Figure 13:
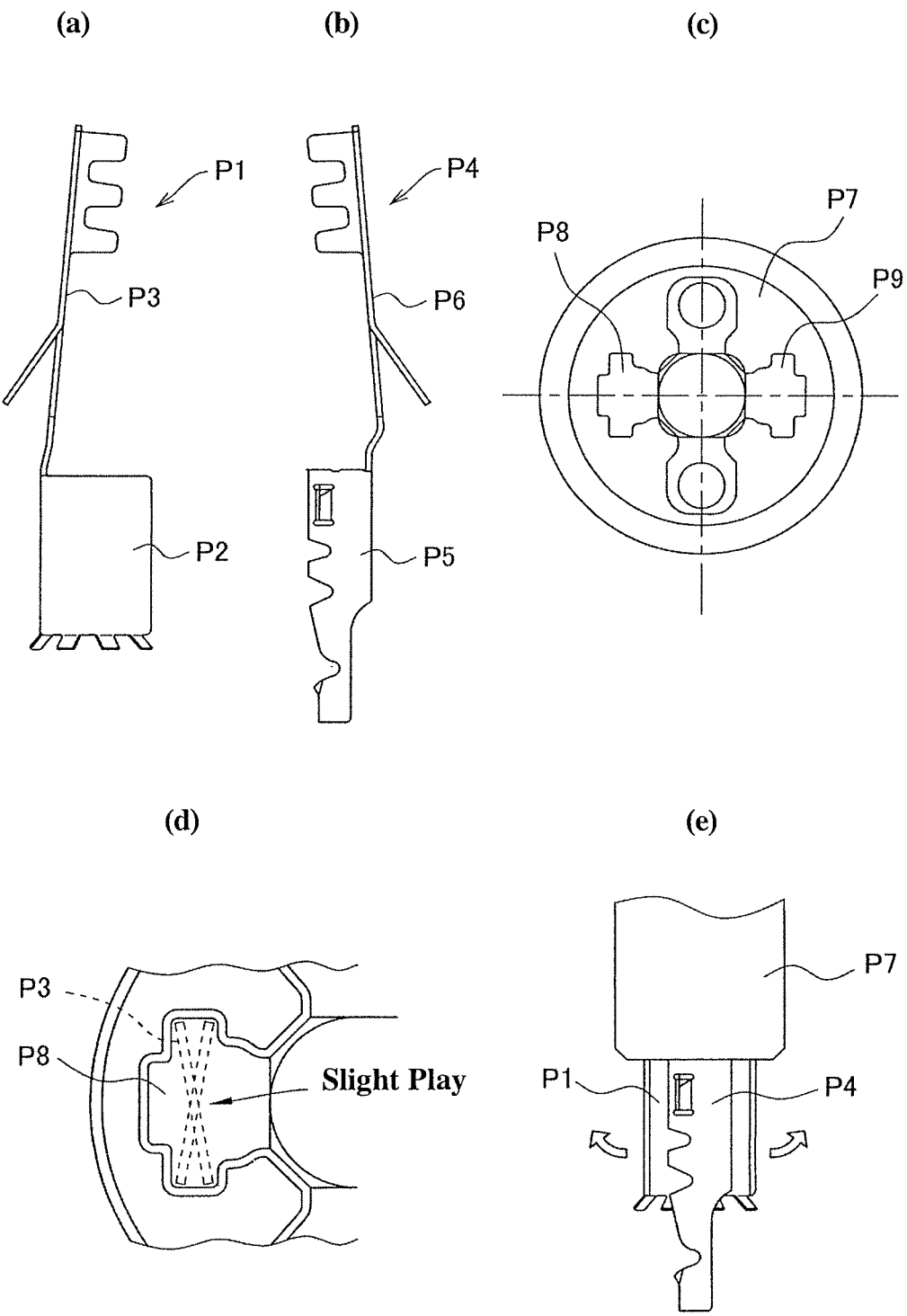
FIG. 13(a) is a perspective view of an outer connection terminal according to the conventional prior art.
FIG. 13(b) is a perspective view of an inner connection terminal according to the conventional prior art.
FIG. 13(c) is a plan view of a front end part of a separator according to the conventional prior art.
FIG. 13(d) is a schematic view showing the vicinity of a through hole in the separator according to the conventional prior art.
FIG. 13(e) is a schematic view of a front end portion of a subassembly unit according to the conventional prior art.

(1) For example, it is feasible to alternatively use a separator 241 shown in FIG. 12 in the fourth embodiment. The separator 241 has an integral protruding portion 249 in which a pair of arc-shaped protruding pieces 243 and 245 are coupled together by a coupling portion 247. This leads to the advantage that the separator 241 can secure toughness.

(2) Although the lateral surface of the protruding portion extends in parallel with the axial direction of the gas sensor in each of the above embodiments, the lateral surface of the protruding portion may be inclined toward the (radially) outside or inside with respect to the axial direction of the gas sensor. Thus, the shape of the protruding portion is not limited to the column shape or prism shape. The protruding portion may be formed into a conical frustum shape or pyramidal frustum shape (increasing or decreasing in width toward the front). Alternatively, the protruding portion may have a lateral surface with a radial protrusion, rather than a flattened lateral surface, such that the outer fitting portion of the outer connection terminal or the inner fitting portion of the inner connection terminal is brought into contact with and fixed to a distal end of the protrusion.

DESCRIPTION OF REFERENCE NUMERALS 1, 201: Oxygen sensor
3, 203: Sensor element
23, 25, 93, 95, 123, 125, 127, 129, 153, 155, 157, 159, 211, 213: Through hole
27, 121, 151, 215, 241: Separator
29, 143, 169, 217: Outer connection terminal
31, 147, 173, 219: Inner connection terminal
53, 145, 171, 231: Outer fitting portion
73, 149, 175, 133: Inner fitting portion
55, 75: Extension portion
61, 81: Cut
105, 107, 109, 111, 131, 133, 135, 137, 161, 163, 165, 167, 227, 119, 249:
Protruding portion
177, 179, 181, 183: Rotation preventing portion

The invention claimed is:

1. A gas sensor subassembly unit for use in manufacturing a gas sensor, the gas sensor comprising: a cylindrical sensor element; a connection terminal located on a rear end side of the sensor element and held in contact with an electrode of the sensor element; and a separator located rear of the sensor element and having a through hole in which a rear end part of the connection terminal is inserted, wherein the gas sensor subassembly unit comprises the connection terminal and the separator integrally mounted together, wherein the connection terminal has a cylindrical fitting portion formed on a front end part thereof so as to be fitted to the sensor element and brought into contact with the electrode of the sensor element and an extension portion formed on a rear end part thereof so as to extend rearward from the fitting portion and be inserted in the through hole of the separator;

wherein the separator has a protruding portion formed on a surface of a front end part thereof so as to protrude frontward; and wherein the fitting portion of the connection terminal is fixed to a radially lateral surface of the protruding portion under the action of a biasing force of the fitting portion.

2. The gas sensor subassembly unit according to claim 1, wherein one or two or more protruding portions are formed on the surface of the front end part of the separator.

3. The gas sensor subassembly unit according to claim 1, wherein the connection terminal is adapted to be fitted onto the sensor element in such a manner as to satisfy the condition: an inner diameter of the fitting portion of the connection terminal (before fixed to the protruding portion) is less than an outer diameter of the protruding portion which is less than an outer diameter of the sensor element.

4. The gas sensor subassembly unit according to claim 1, wherein the connection terminal is adapted to be fitted into the sensor element in such a manner as to satisfy the condition: an inner diameter of the sensor element is less than an inner diameter of the protruding portion which is less than an outer diameter of the fitting portion of the connection terminal (before fixed to the protruding portion).

5. The gas sensor subassembly unit according to claim 1, wherein a cut is formed axially in the fitting portion of the connection terminal such that the fitting portion is divided into circumferentially opposite sections by the cut.

6. The gas sensor subassembly unit according to claim 1, wherein the separator has a rotation preventing portion protruding frontward from the surface of the front end part thereof at a position along a rotational direction of the fitting portion of the connection terminal so as to prevent rotation of the fitting portion.

7. A gas sensor comprising: a cylindrical sensor element; and the gas sensor subassembly unit according to claim 1, the fitting portion of the connection terminal of the gas sensor assembly unit being fitted to the sensor element.

8. The gas sensor subassembly unit according to claim 1, wherein the protruding portion comprises a plurality of protruding portions.

9. The gas sensor subassembly unit according to claim 1, wherein the protruding portion comprises two or four protruding portions.

10. The gas sensor subassembly unit according to claim 8, wherein the plurality of protruding portions are arranged at circumferentially spaced positions.

11. The gas sensor subassembly unit according to claim 1, wherein the gas sensor subassembly unit comprises a plurality of through holes.

12. The gas sensor subassembly unit according to claim 11, wherein a plurality of protruding portions are arranged at circumferentially spaced positions between the through holes about the center axis of the separator.

13. The gas sensor subassembly unit according to claim 8, wherein each of the protruding portions has two structural members such that the structural members of the protruding portions are doubled concentrically about the center axis of the separator.

14. The gas sensor subassembly unit according to claim 1, wherein a cross section of the protruding portion in the axial direction does not extend around the entire circumference of the separator.

\* \* \* \* \*